(12) United States Patent
Oak et al.

(10) Patent No.: US 8,734,866 B2
(45) Date of Patent: May 27, 2014

(54) **COMPOSITION COMPRISING THE EXTRACTS OF *LINDERA OBTUSILOBA* FOR PREVENTION AND TREATMENT OF CARDIOVASCULAR DISEASES**

(75) Inventors: Min-Ho Oak, Gyeonggi-do (KR); Jung-Ok Lee, Gyeonggi-do (KR); Woon-Sun Choi, Ulsan (KR); Jung-Duk Sohn, Gyeonggi-do (KR); Jong-Hoon Kim, Gyeonggi-do (KR); Jee Woong Lim, Gyeonggi-do (KR); Chung Keun Rhee, Seoul (KR)

(73) Assignees: Yang Ji Chemical Co., Ltd. (KR); Han Wha Pharma Co., Ltd. (KR)

( * ) Notice: Subject to any disclaimer, the term of this patent is extended or adjusted under 35 U.S.C. 154(b) by 20 days.

(21) Appl. No.: 12/863,368

(22) PCT Filed: Dec. 17, 2008

(86) PCT No.: PCT/KR2008/007484
§ 371 (c)(1),
(2), (4) Date: Oct. 18, 2010

(87) PCT Pub. No.: WO2009/091120
PCT Pub. Date: Jul. 23, 2009

(65) Prior Publication Data
US 2011/0045111 A1 Feb. 24, 2011

(30) Foreign Application Priority Data
Jan. 18, 2008 (KR) .................. 10-2008-0005672

(51) Int. Cl.
*A61K 36/00* (2006.01)
(52) U.S. Cl.
USPC ........................... 424/774; 424/725; 424/779
(58) Field of Classification Search
None
See application file for complete search history.

(56) References Cited

U.S. PATENT DOCUMENTS

| 5,135,746 A * | 8/1992 | Matsuno et al. ............... 424/725 |
| 5,902,831 A | 5/1999 | Holland et al. |
| 2007/0160699 A1 | 7/2007 | Kim |

FOREIGN PATENT DOCUMENTS

| CN | 001742801 | 3/2006 |
| CN | 1742801 | 3/2006 |
| JP | 06-135830 | 5/1994 |
| JP | 2000-344673 | 12/2000 |
| JP | 2000344673 | 12/2000 |
| KR | 10-2001-0015807 | 2/2001 |
| KR | 10-2001-0042815 | 5/2001 |
| KR | 10-2002-0084230 | 11/2002 |
| KR | 10-2003-0041965 | 5/2003 |
| KR | 10-2003-0055276 | 7/2003 |
| KR | 10-2003-0086340 | 7/2003 |
| KR | 10-2006-0027830 | 3/2006 |
| KR | 10-2006-0135950 | 12/2006 |
| KR | 10-2007-0050998 | 5/2007 |
| KR | 10-0732888 | 6/2007 |
| KR | 10-2009-0079650 | 7/2009 |

OTHER PUBLICATIONS

Park, J-C., Yu, Y-B., Lee, J-H (1996) Isolation and Structure Elucidation of Flavonoid Glycosides from *Lindera obtusiloba* BL. J. Korean Soc. Food Nutr. 25(1), 76-79.*
Ja Panza et al., "Abnormal endothelium-dependent vascular relaxation in the patients with essential hypertension," The New England Journal of Medicine, vol. 323, Jul. 5, 1990, pp. 22-27.
Hanspeter Brunner et al., "Endothelial function and dysfunction. Part II: Association with cardiovascular risk factors and disease. A statement by the Working Group on Endothelins and Endothelial Factors of the European Society of Hypertension," Journal of Hypertension, vol. 23, No. 2, 2005, pp. 233-246.
Ulrich Forstermann et al., "Endothelial Nitric Oxide Synthase in Vascular Disease: From Marvel to Menace," Circulation, Jul. 12, 2010.
R. J. Gryglewski et al., "Superoxide anion is involved in the breakdown of endothelium-derived vascular relaxing factor," Nature Publishing Group, vol. 320, Apr. 3, 1986, pp. 454-455.
Chang-Bok Lee, "Illustrated Book of Korean Plants," 1980, p. 403.
Jong-Hee Park, "Illustrated Book of Korean Folk Medicines," 2005, p. 256.
Bo-Seop Jeong et al,m, Encyclopedia of Local Medicines (Plant), 1990, p. 458.
Jong-Cheol Park et al., "Isolation and Structure Elucidation of Flavonoid Glycosides from *Lindera obtusiloba* BL," J. Korean Soc. Food Nutr., vol. 25, No. 1, 1996, pp. 76-79.
Search Output of endothelial dysfunction (ClinicalTrials.gov).
Results on Map: endothelial dysfunction (ClinicalTrials.gov).
Search Output of Nafronyl oxalate (KIMS).
Tamara M. Paravicini et al., Increased NADPH Oxidase Activity, gp91phox Expression, and Endothelium-Dependent Vasorelaxation During Neointima Formation in Rabbits, Circres, Jul. 12, 2010.
Gregory J. Dusting et al., "Nitric Oxide in Atherosclerosis: Vascular Protector or Villain?," Clinical and Experimental Pharmacology and Physiology, vol. 25, 1998, pp. S34-S41.
S. K. Lo et al., "Hydrogen peroxide-induced increase in endothelial adhesiveness is dependenton ICAM-1 activation," AMJ-Lung Cellular and Molecular Physiology, vol. 264, Issue 4 406-L412, 1993.
Kathy K. Griendling et al., "Redox control of vascular smooth muscle proliferation," J Lab Clin Med, vol. 132, Jul. 1998, pp. 9-15.
Sean M. Lynch et al., "Mechanisms of copper-and iron-dependent oxidative modification of human low density lipoprotein," Journal of Lipid Research, vol. 34, 1993, pp. 1745-1753.
Tomasz J. Guzik et al., Vascular Superoxide Production by NAD(P)H Oxidase: Association With Endothelial Dysfunction and Clinical Risk Factors, Circ Res., vol. 86, 2000, pp. e85-e90.
Sheila A. Doggrell, "New Drugs and New Targets" Drug News Perspect, vol. 17, No. 9, 2004, pp. 615.

(Continued)

*Primary Examiner* — Chris R Tate
*Assistant Examiner* — Russell Fiebig
(74) *Attorney, Agent, or Firm* — Cantor Colburn LLP (57) ABSTRACT

The present invention relates to a composition for treatment and prevention of cardiovascular diseases, containing an extract of *Lindera obtusiloba*. More particularly, the extract of *Lindera obtusiloba* strongly inhibits NAD(P)H oxidases, which are the main cause of vascular diseases, and at the same time, regulates contraction and relaxation of vascular smooth muscles to manifest a potent vasorelaxant effect, thereby improving the blood pressure regulation and vascular endothelial dysfunction. Therefore, a composition containing this as an active ingredient can be usefully utilized as a pharmaceutical product or health functional food product for the prevention and treatment of cardiovascular diseases.

11 Claims, 4 Drawing Sheets

(56) References Cited

OTHER PUBLICATIONS

Toyoshi Inoguchi et al., "NAD(P)H Oxidase Activation: A Potential Target Machanism for Diabetic Vascular Complications, Progressive B-Cell Dysfunction and Metabolic Syndrome,"Current Drug Targets, vol. 6, No. 4, 2005, pp. 495-501.

Saima Muzaffar et al., "Nicotinamide Adenine Dinucleotide Phosphate Oxidase: A Promiscuous Therapeutic Target for Cardiovascular Drugs," TCM, vol. 15, No. 8, 2005, pp. 278-282.

Hak Cheol Kwon et al., "Two New Lignans from *Lindera obtusiloba* Blume," Arch Pharm Res., vol. 22, No. 4, 1999, pp. 417-422.

Hyun-Ju Jung et al., "In vivo Anti-Inflammatory and Antinociceptive Effects of Liriodendrin Isolated from the Stem Bark of *Acanthopanax senticosus*," Planta Med, vol. 69, 2003, pp. 610-616.

J.B. Harborne, "Methods of plant analysis," Phytochemical methods: A guide to modern techniques of plant analysis, 3rd Edition, 1998, pp. 6-7.

Yi Shi et al., "Increased NAD(P)H Oxidase and Reactive Oxygen Species in Coronary Arteries After Balloon Injury," Arteriosclerosis, Thrombosis, and Vascular Biology, vol. 21, 2001, pp. 739-745.

Karen Y. Stokes et al., "NAD(P)H Oxidase-Derived Superoxide Mediates Hypercholesterolemia-Induced Leukocyte-Endothelial Cell Adhesion," Circulation Research, vol. 88, 2001, pp. 499-505.

F.E. Rey et al., "Novel Competitive Inhibitor of NAD(P)H Oxidase Assembly Attenuates Vascular O 2-and Systolic Blood Pressure in Mice," Circulation Research,vol. 89, Aug. 31, 2001, pp. 408-414.

Patricia A. Barry-Lane et al., "p47phox is required for atherosclerotic lesion progression in ApoE-/- mice," The Journal of Clinical Investigation, vol. 108, No. 10, Nov. 2001, pp. 1513-1522.

Katalin Szocs et al., "Upregulation of Nox-Based NAD(P)H Oxidases in Restenosis After Carotid Injury," Arteriosclerosis Thrombosis, and Vascular Biology, vol. 22, 2002, pp. 21-27.

Tamara M. Paravicini et al., "Redox signaling in hypertension," Cardiovascular Research, vol. 71, Jul. 15, 2006, pp. 247-258.

L. Loffredo et al., "Oxidative-stress-mediated arterial dysfunction in patients with peripheral arterial disease," European Heart Journal, vol. 28, 2007, pp. 608-612.

Carlene A. Hamilton et al., Superoxide Excess in Hypertension and Aging a common Cause of Endothelial Dysfunction, Hypertension, vol. 37, 2001, pp. 529-534.

Akiko Fukatsu et al., "Possible usefulness of apocynin, an NADPH oxidase inhibitor, for nitrate tolerance: prevention of NO donor-induced endothelial cell abnormalities,"Am J Physiol Heart Circ Physiol, vol. 293, 2007, pp. H790-H797.

Ascan Warnholtz et al., "Increased Nadh-Oxidase-Mediated Superoxide Production in the Early Stages of Atherosclerosis: Evidence for Involvement of the Renin-Angiotensin System," Circulation, vol. 99, 1999, pp. 2027-2033.

Alison C. Cave et al., "NADPH Oxidase in Cardiovascular Health and Disease," Antioxidants & Redox Signaling, vol. 8, No. 5 & 6, 2006, pp. 691-728.

Peripheral vascular disease, http://en.wikipedia.org/wiki/Peripheral_vascular_disease2002.

Peter C. Wyer et al., "Vasopressin or Epinephrine for Out-of-Hospital Cardiac Arrest," Annals of Emergency Medicine, vol. 48, No. 1, Jul. 2006, pp. 86-97.

"Overweight and Obesity Statistics," NIH, 2010.

"Clinical Vascular Medicine," The Korean Society of Cardiology, 2009.

http://www.medii.co.kr/data/main_data_dise2.asp?scode=100-199.

Bo Ram Koh et al., "Relationship between Diabetic Peripheral Vascular Disease and Ankle-Brachial Index," J. Korean Endocrine Soc.:, vol. 21, No. 5, 2006, pp. 382-388.

Discription of RIDUCTIL, Abbott GmbH & Co. KG).

Description of Riptown (Hanmi Pharm.).

Kisam Chung,"Outline of HRV," J. Korean Acad Fam Med, vol. 25, No. 11, 2004, pp. S528-S532.

Judy W.M. Cheng et al., "A Review of Heart Failure Management in the Elderly Population," The American Journal of Geriatric Pharmacotherapy, vol. 7, No. 5, Oct. 2009, pp. 233-249.

Youngsook Kang et al., "Human Physiology," Life Science, 5th edition, 2005.

Ulrich Forstermann et al., "Endothelial Nitric Oxide Synthase in Vascular Disease: From Marvel to Menace," Circulation. vol. 113, 2006, pp. 1708-1714.

M. K. Na, et al, Antioxidant Effects of Plant Extracts on Free Radicals and Lipid Peroxidation, Natural Product Sciences, 2003, pp. 226-231.

Philippine Substantive Examination Report—Philippine Application No. 1/2010/501596 issued on Apr. 17, 2013, citing Database TCM(Online) SIPO, Jong-Cheol Park et al, Ruehl et al. And Kwon H C et al.

J. C. Park et al., Isolation and Structure Elucidation of Flavonoid Glycosides from *Lindera obtusiloba* BL., J. Korean Soc. Food Nutr., 1996, pp. 76-79.

M. Ruehl et al., Antibrotic Effects of *Lindera obtusiloba* Extracts: Downregulation of TGF-Beta Induced Collagen Type I Expression and Neutralization of Peroxide Induced ROS Production in Hepatic Stellate Cells, Molecular and Cellular Biology, 2007 pp. 132-133.

H. C. Kwon et al., Two New Lignans from *Lindera obtusiloba* Blume, Arch Pharm Res., 1999, pp. 417-422.

European Search Report-European Application No. 08 87 0964 issued Mar. 25, 2011.

M. Ruehl et al., "Antifibrotic Effects of *Lindera Obtusiloba* Extracts: Downregulation of TGF-B Induced Collagen Type I Expression and Neutralization of Peroxide Induced Pros Production in Hepatic Stellate Cells," Journal of Hepatology, Munksgaard International Publishers, Copenhagen, DK, vol. 46, Apr. 1, 2007, pp. S132-S133.

Kwon H C et al., "Two new lignans from *Lindera obtusiloba* blume", Medline, Aug. 1, 1999, p. 1.

Zhang Yiqun, "A topical medicament of Herba Vaccinii Urophylli/ A topical pharmaceutical composition of treatment of herba Vaccinii Urophylli for treating rheumatic arthralgia, traumatic blood stasis and pain, and soft tissue contusion, ect.," Database TCM(online), Mar. 8, 2006.

\* cited by examiner

CRUDE TWIG EXTRACT OF LINDERA OBTUSILOBA

COMPOSITION COMPRISING THE EXTRACTS OF *LINDERA OBTUSILOBA* FOR PREVENTION AND TREATMENT OF CARDIOVASCULAR DISEASES

TECHNICAL FIELD

The present invention relates to a composition for prevention and treatment of cardiovascular diseases, which comprises an extract of *Lindera obtusiloba*, and health functional food products. More particularly, the invention is characterized by containing, as an active ingredient, an extract of *Lindera obtusiloba* which has an effect of treating and preventing cardiovascular diseases by directly inhibiting NAD(P)H oxidases to suppress oxidative stress, and at the same time, activating endothelial-type nitric oxide synthase to thereby regulate the contraction and relaxation of vascular smooth muscle cells.

BACKGROUND ART

According to the statistics of the World Health Organization (WHO), it is reported that the world death rate for cardiovascular diseases in 1999 was 30% or greater, and the cardiovascular diseases will be the first ranking diseases causing death in developed countries in year 2010, while the increase rate of the diseases is high particularly in Asian countries including Japan, South Korea and the like. This is speculated to be attributable to an increase in the risk factors for coronary artery diseases, as a result of the coming aged society, changes in the dietary habits, and the like.

Endothelial dysfunction is the main mechanism which induces an extensive range of cardiovascular diseases, including hypertension, arteriosclerosis, hyperlipidemia, diabetes mellitus, obesity and the like (Brunner H. et al., J. Hypertens., 2005, 23:233-246), since the discovery of abnormal relaxation of blood vessels in hypertensive patients in 1990 (Panza J A et al., New England Journal of Medicine, 323:22-27, 1990). Endothelial cells are epithelial cells lining along the cavities of blood vessels and lymph vessels, and their main function is to produce vasodilators and vasodilator mediators to regulate the vascular tone as well as the structure.

A cardiovascular disease is a disease starting in the form of initial endothelial dysfunction and finally resulting in abnormality in the heart and vascular system. The name is a generic term for a group of abnormalities in the heart and blood vessels, including, but not limited to, arteriosclerosis, hypertension, hyperlipidemia, coronary artery diseases (heart attack), cerebrovascular diseases (cerebral stroke, dementia), peripheral vascular diseases, arrhythmia, cardiac failure, congestive heart diseases, myocardial diseases, and the like.

As for principal factors for the manifestation of cardiovascular diseases, there are known a variety of factors such as genetic factors, lifestyle, and complications of diabetes mellitus. From the standpoint of modern medicine, increases in the reactive oxygen species (ROS) and vascular oxidative stress as a result of an increase in the activity of NADPH oxidases, and a decrease in nitric oxide due to a decrease in the activity of endothelial-type nitric oxide synthase (eNOS), are known as principal factors. Nitric oxide which is produced by endothelia-type nitric oxide synthase, is a potent vasorelaxant factor, and also plays a critical role in the overall homeostatic regulation of the cardiovascular system by inhibiting platelet aggregation, proliferation of vascular muscle cells, vascular adhesion of monocytes, and expression of arteriosclerosis-associated proteins (Forstermann et al., Circulation, 113:1708-1714, 2006). However, an increase, caused by a number of factors, in the activity of NADPH oxidases which are in charge of the generation of active oxygen species in the blood vessels, leads to a decrease in the production of nitric oxide [Gryglewski et al., Nature, 320: 454-456, 1986; Paravicini et al., Circulation Research, 91:54-61, 2002; Dusting et al., Clinical and Experimental Pharmacology and Physiology, 25:S34-41, 1998], and the active oxygen species thus produced bring about regulation of the expression of adhesive molecules [Lo et al., Am. J. Physiol., 264:L406-412, 1993], stimulation of the proliferation and migration of vascular smooth muscle cells (VSMC) [Griendling and Ushio-Fukai, J. Lab. Clin. Med., 132:9-15, 1998], regulation of lipoproteins having oxidizing power, and the like, to thereby cause cardiovascular diseases [Lynch and Frei, J. Lipid Res., 34:1745-1753, 1993]. Furthermore, the increased generation of active oxygen species in the blood vessels due to NAD(P)H oxidases, is associated with the impaired function of endothelial nitric oxide (NO) in patients having clinical risk factors for atherosclerosis and coronary artery diseases. Fundamentally, the generation of active oxygen species brings about contraction of blood vessels [Guzik et al., Cir. Res., 86:E85-90, 2000]. In general, reduction of active oxygen species, suppression of downstream generation of active oxygen species, and induction of the activity of endothelial-type nitric oxide synthase, all through direct inhibition of NAD(P)H oxidases, are recognized as very important targets in the prevention and treatment of cardiovascular diseases [Forstermann et al., Circulation, 113:1708-1714, 2006; Doggrell S A, Drug News Perspect., 17(9) 615-632, 2004; Inoguchi T., Curr. Drug Targets, 6(4):495-501, 2005; Muzaffar S. et al., Trends Cardiovasc Med., 15(8):278-282].

To date, known as the substances inhibiting NAD(P)H oxidases are diphenylene iodonium (DPI) and 4-hydroxy-3-methoxyacetophenone (Apocynin) [Holland J, et al., U.S. Pat. No. 5,902,831]. However, these substances have not been put into commercialization or clinical use because of the problems of toxicity and specificity. Furthermore, as nitric oxide regulators, there are available nitroprusside and nitroglycerine. However, these substances are also put into use only in the cases of emergency such as heart attack, because of the problems of resistance and toxicity in clinical uses.

Meanwhile, *Lindera obtusiloba* is a deciduous shrub of family Lauraceae. It grows to a height of about 2 to 3 m, and the flowering season is from March to April, while the fruiting season is September. The fruits are pressed to obtain oil, which has been used as a hair oil for women. The plant is called "Ginger Tree" because the plant smells like ginger when the leaves or twigs are plucked off, and is also known as Fool's Camellia or Japanese spicebush. The plant is known to be efficacious in activation of blood, slow twitching of muscle, anti-abscess and the like, and to treat bruises, and swelling and pain due to blood extravasation, and the plant is usually squashed and adhered to the site of wound. The plant is mainly used against stomach ache, and is also used as an antifebrile or a cough medicine. In private practices, leaves and buds of the plant are brewed and taken like tea, as an antifebrile or a cough medicine [Illustrated Book of Korean Plants, by Chang-Bok Lee, 1980; Illustrated Book of Korean Folk Medicines, by Jong-Hee Park, 2005, Encyclopedia of Local Medicines].

In regard to researches on the components of *Lindera Obtusiloba*, Park, Jong-Chul, et al. (J. Korean Soc. Food Nutr. 1996. 25(1), p. 76-79) isolated quercitrin from the leaves, and hyperoside from the twigs, while Kwon, Hak-Cheol, et al. (Archives of Pharmacal Research, 22, p. 417-422, 1999) isolated actifolin, pluviatiolol, 5,6-dihydromatairesinol, (+)-syringaresinol, 9-O-trans-feruloyl-5,5-dimethoxylariciresinol and the like. The efficacies of the respective isolated components are reported to include cancinocidal action, anti-inflammatory action, and the like (Planta Medica, 69, 610-616, 2003; Archives of Pharmacal Research, 22, p. 417-422, 1999).

However, no disclosure or teaching is given in the above-mentioned literatures, on that an extract of *Lindera obtusiloba* has effects of suppression of vascular oxidative stress, relaxation of blood vessels and regulation of blood pressure, through inhibition of NADPH oxidases.

DISCLOSURE OF THE INVENTION

Technical Problem

Thus, the inventors of the present invention conducted an investigation on the inhibition of NAD(P)H oxidase activity and vasorelaxant effect with a number of plant extracts, and finally confirmed the effects of potent inhibition of the activity of NAD(P)H oxidases, reduction of vascular oxidative stress, direct enhancement of the activity of endothelial type nitric oxide synthase, relaxation of blood vessels and regulation of blood pressure, thus completing the present invention.

The present invention was designed to solve the problems such as described above, and an object of the invention is to provide a composition for prevention and treatment of a cardiovascular disease, comprising an extract of *Lindera obtusiloba* as an active ingredient.

Another object of the present invention is to provide a health functional food product for prevention of a cardiovascular disease, comprising an extract of *Lindera obtusiloba* as an active ingredient.

Technical Solution

To achieve the objects as described above, the composition for prevention and treatment of a cardiovascular disease of the present invention is characterized by containing an extract of *Lindera obtusiloba* as an active ingredient.

The extract of *Lindera obtusiloba* is preferably an extract obtained from the twigs, the leaves, or the twigs and leaves.

The extract of *Lindera obtusiloba* is preferably extracted with a solvent selected from the group of water, a C1-C5 lower alcohol, and a mixture thereof.

The extract of *Lindera obtusiloba* is preferably extracted with a 30 to 95 wt % aqueous solution of ethanol.

It is preferable that the extract of *Lindera obtusiloba* be extracted with a solvent selected from the group of water, a C1-C5 lower alcohol and a mixture thereof, and the extract be re-extracted with butanol.

The extract of *Lindera obtusiloba* is characterized by having an NAD(P)H oxidase inhibitory activity.

The extract of *Lindera obtusiloba* is characterized by having a vasorelaxant effect.

The extract of *Lindera obtusiloba* is characterized by an effect of enhancing the activity of endothelial-type nitric oxide synthase.

The extract of *Lindera obtusiloba* is characterized by having effects of decreasing the blood pressure and reducing the vascular oxidative stress.

The cardiovascular disease may be selected from the group consisting of congestive heart diseases, coronary artery diseases (heart attack), ischemic heart diseases (myocardial ischemia), hyperlipidemia, arteriosclerosis, hypertension, hypotension, arrhythmia, cardiac failure, vascular restenosis, cerebrovascular diseases (cerebral stroke, dementia), peripheral vascular diseases and metabolic diseases.

Meanwhile, the health functional food product for prevention of a cardiovascular disease of the present invention is characterized by containing an extract of *Lindera obtusiloba* as an active ingredient.

Advantageous Effects

As discussed in the above, the extract of *Lindera obtusiloba* of the present invention strongly inhibits the activity of NAD(P)H oxidases and exhibits a vasorelaxant effect at the same time, and thus can be usefully utilized as a pharmaceutical composition or health functional food product for prevention and treatment of a cardiovascular disease.

BEST MODE FOR CARRYING OUT THE INVENTION

Hereinafter, preferred embodiments of the present invention will be described in detail. In the following description, numerous characteristic terms such as specific constituent elements are illustrated, but these are provided only for the purpose of providing an aid for more comprehensive understand of the present invention, and it will be obvious to those having ordinary skill in this technical field that the present invention can be carried out even without these characteristic terms. Furthermore, in the description of the present invention, if it is judged that specific explanation of any related known function or constitution may unnecessarily make the gist of the invention unclear, the detailed explanation will be omitted.

The extract of *Lindera obtusiloba* of the present invention can be obtained as follows.

The aerial part, more specifically, the leaves and twigs, of *Lindera obtusiloba* can be used without limitation, in the form of plants collected from nature, cultivated plants, commercially available plants, or the like. The solvent for extraction is selected from the group consisting of water, a C1-C5 lower alcohol, and a mixture thereof. The inventors of the present invention washed the twigs and leaves of *Lindera obtusiloba* to remove impurities and salts, and dried them. Subsequently, extraction was performed with a polar solvent such as water or a C1-C5 lower alcohol such as methanol, ethanol or butanol, or a mixed solvent of these at a mixing ratio of about 1:0.1 to 1:10, preferably with a to 95 wt % aqueous solution of ethanol, in a volume reaching about 5- to 50-fold, and preferably 10- to 30-fold, the weight of the

*Lindera obtusiloba* sample, at 50 to 95°C for 1 hour to 7 days. The above-described extraction process is repeated two or five times, and preferably three times, and then the resultant is subjected to concentration under reduced pressure and/or freeze-drying, to obtain a crude extract of *Lindera obtusiloba*.

Among the extracts of the present invention, a non-polar solvent-soluble extract can be obtained by suspending the aforementioned crude extract in distilled water, subsequently adding a non-polar solvent such as hexane, ethyl acetate or chloroform in a volume of about 0.1 to 100 times, and preferably about 1 to 5 times, the volume of the suspension, and performing extraction and isolation once to 10 times, and preferably two to five times. Furthermore, conventional fractionation processes can also be additionally carried out (Harborne, J. B., Phytochemical methods: A guide to modern techniques of plant analysis, 3rd Ed., pp. 6-7, 1998).

More preferably, the crude extract of *Lindera obtusiloba* obtained by the above-described processes, preferably an extract of *Lindera obtusiloba* in an aqueous solution of ethanol, is subjected to sequential solvent fractionation with organic solvents such as n-butanol, hexane and ethyl acetate, in order from less polar solvent to more polar solvent, preferably in order of hexane, ethyl acetate and n-butanol, and to concentration under reduced pressure, and thus hexane, ethyl acetate and n-butanol fractions of *Lindera obtusiloba* can be obtained.

The present invention provides a composition for prevention and treatment of a cardiovascular disease, which comprises the crude extract or non-polar solvent-soluble extract of *Lindera obtusiloba* obtained by the above-described production method, as an active ingredient.

The composition for prevention and treatment of a cardiovascular disease according to the present invention contains 0.1 to 99% by weight of the aforementioned extract based on the total weight of the composition.

The composition containing the extract of *Lindera obtusiloba* of the present invention may further contain appropriate carriers, excipients and diluents that are conventionally used in the production of compositions.

The pharmaceutical dosage form of the extract of the present invention can be used in the form of pharmaceutically acceptable salts thereof, and also can be used alone, or in the form of conjugate as well as appropriate assembly with other pharmaceutically active compounds.

The pharmaceutical composition containing the extract according to the present invention can be used after being formulated into oral formulations such as powders, granules, tablets, capsules, suspensions, emulsions, syrups and aerosols, and into topical formulations, suppositories and sterile injectable solutions, respectively according to conventional methods.

As for the carriers, excipients and diluents that can be contained in the composition containing the extract, there may be mentioned lactose, dextrose, sucrose, sorbitol, mannitol, xylytol, erythritol, maltitol, starch, acacia gum, alginate, gelatin, calcium phosphate, calcium silicate, cellulose, methylcellulose, non-crystalline cellulose, polyvinylpyrrolidone, water, methylhydroxybenzoate, propylhydroxybenzoate, talc, magnesium stearate, and mineral oil.

In the case of formulating into preparations, they are prepared using conventionally used diluents or excipients, such as fillers, bulking agents, binding agents, wetting agents, disintegrants and surfactants.

Examples of solid preparations for oral administration include tablets, pills, powders, granules, capsules and the like, and these solid preparations are prepared by mixing at least one excipient, for example, starch, calcium carbonate, sucrose or lactose, gelatin and the like to the aforementioned extract. Furthermore, in addition to simple excipients, lubricants such as magnesium stearate and talc are also used.

Examples of liquid preparations for oral administration include suspensions, liquids for internal use, emulsions, syrups and the like. These liquid preparations may include various excipients, for example, wetting agents, sweeteners, fragrances, preservatives and the like, in addition to water and liquid paraffins, which are frequently used simple diluents.

Examples of preparations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like can be used. As the base of the suppositories, witepsol, Macrogol, Tween, cacao butter, laurin fat, glycerogelatin and the like can be used.

A preferable amount of administration of the extract of the present invention may vary with the condition and weight of the patient, severity of the disease, form of drug, the route and period of administration, but can be appropriately selected by a person having ordinary skill in the art. However, for preferable effects, it is desirable to administer the extract of the present invention in an amount of 0.0001 to 100 mg/kg, and preferably 0.001 to 100 mg/kg, per day. Administration may be carried out once a day, or may be carried out several times a day. The amount of administration is not intended to limit the scope of the invention by any means.

The present invention provides a health functional food product containing the aforementioned extract showing an effect of preventing a cardiovascular disease, and sitologically acceptable food additives.

As for the health functional food products which can be added with an extract of *Lindera obtusiloba*, for example, there may be mentioned various general food products, beverages, chewing gums, tea, vitamin complexes, and the like.

The extract of *Lindera obtusiloba* can also be added to foods or beverages for the purpose of obtaining an effect of preventing a cardiovascular disease. In this case, the amount of the extract in a food product or beverage may be 0.01 to 15% by weight based on the total weight of the food. The amount of the extract in a health beverage composition may be 0.02 to 5 g, and preferably 0.3 to 1 g, relative to 100 g of the total weight of the beverage.

The health functional beverage composition of the present invention is not particularly limited in containing other components, in addition to containing the extract as an essential component at the indicated proportions, and can contain additional components such as various flavoring agents or natural carbohydrates, as conventional beverages do. Examples of the aforementioned natural carbohydrates include conventional saccharides, such as monosaccharides, for example, glucose, fructose and the like; disaccharides, for example, maltose, sucrose and the like; and polysaccharides, for example, dextrin, cyclodextrin and the like, and sugar alcohols such as xylytol, sorbitol and erythritol. As the flavoring agents in addition to the aforementioned agents, thaumatin, stevia extracts, for example, levaudioside A, glycyrrhizin and the like; and synthetic flavoring agents, for example, saccharin, aspartame and the like can be advantageously used. The proportion of the natural carbohydrates is generally about 1 to 20 g, and preferably about 5 to 12 g, per 100 g of the composition of the present invention.

In addition to these, the extract of the present invention may contain various nutrients, vitamins, minerals (electrolytes), synthetic and natural flavoring agents, colorants and weighting agents (cheese, chocolate and the like), pectic acid and salts thereof, alginic acid and salts thereof, organic acids, protective colloidal thickeners, pH adjusting agents, stabilizers, antiseptics, glycerin, alcohols, carbonating agents used in carbonated drinks, and the like. In addition thereto, the extracts of the present invention may contain natural fruit juices, and fruit fleshes for the production of fruit juice beverages and vegetable beverages. These components can be used individually or in combinations. In this case, the proportion of the additives is not critical, but is generally selected from the range of 0.01 to about 20 parts by weight per 100 parts by weight of the extract of the present invention.

Hereinafter, the present invention will be described more specifically, by making reference to the following Examples and Test Examples.

EXAMPLES

Example 1

Preparation of Crude Extract of *Lindera obtusiloba*

The twigs and leaves of *Lindera obtusiloba* collected in Kangwon-do Province were washed with water to remove impurities and salts, and then were dried and crushed. In an extraction vessel, 25 g each of the crushed twigs or the crushed leaves of *Lindera obtusiloba*, and 500 ml in total of a 70 wt % aqueous solution of ethanol were added, and thermal extraction was repeatedly performed three times at 70°C, each time taking 3 hours, under reflux cooling. The resultant was filtered through a filter paper, and the filtrate was concentrated under reduced pressure in a water bath at 40°C, and was freeze-dried. As a result, 6.4 g of a crude extract of the twigs of *Lindera obtusiloba* and 7.0 g of a crude extract of the leaves of *Lindera obtusiloba* were obtained.

Example 2

Preparation of Fractions of Crude Extracts of *Lindera obtusiloba*

5 g each of the crude extracts of the leaves and twigs of *Lindera obtusiloba* obtained in Example 1 were respectively suspended in 50 ml of purified water. The resultant was subjected to sequential solvent fractionation three times respectively, with 50 ml each of hexane, ethyl acetate and n-butanol in this order, to obtain the respective solvent fractions, and these were concentrated under reduced pressure. As a result, a hexane fraction, an ethyl acetate fraction and an n-butanol fraction of *Lindera obtusiloba* were obtained.

Test Example 1

Measurement of Inhibitory Effect of Extracts of *Lindera obtusiloba* on NAD(P)H Oxidase Activity The crude extracts and fractions of *Lindera obtusiloba* prepared in Example 1 and Example 2 as described above were subjected to the measurement of an effect of inhibiting the activity of NAD(P)H oxidases, which are index enzymes for the development of cardiovascular diseases. To this end, the arterial smooth muscle cells of white rat (Rat aortic smooth muscle cells; RASMC) and the vascular endothelial cells of calf (Bovine aortic endothelial cells; BAECs) were used to compare the changes in the NADPH oxidase activity, and the results are as shown in the following Table 1. First, the arterial smooth muscle cells and the vascular endothelial cells were respectively mixed with MEM (minimum essential medium), DMEM (Dulbecco's minimum essential medium) and a 10% FBS (fetal bovine serum) solution, and the cells were respectively incubated on a 96-well plate for 24 hours under the conditions of 5% CO2/37°C. Then, the cells were incubated again for 24 hours in the culture solution with FBS excluded. After the cells were stabilized, the cells were washed with HBSS (Hank's balanced salt solution). These cells were shaken with the leaf extract or twig extract of *Lindera obtusiloba* obtained in the Example 1, and then the mixture was allowed to react for 15 minutes and washed again with HBSS. Subsequently, 100 mM NAD(P)H and 5 μM Lucigenin were added to the reaction liquid, and the activity of NAD(P)H oxidases was measured for one hour, using a luminescence reader (Victor Light, PerkinElmer). The test was operated three times, while repeated 2 to 7 times for each operation. Subsequently, the activity of the control group and the activity of the sample-treated group were compared, and the 1050 values were calculated. The 1050 value is the concentration, expressed in μg/ml, of a test material, at which 50% of the NADPH oxidase activity is inhibited.

TABLE 1

Inhibitory effect of extracts of *Lindera obtusiloba* on NADPH oxidase activity (unit: μg/ml)

|  | IC50 (BAECs) | IC50 (RASMC) |
|---|---|---|
| Crude twig extract of *Lindera obtusiloba* | 2.1 | 2.0 |
| Butanol fraction of twigs of *Lindera obtusiloba* | 0.9 | 1.5 |
| Ethyl acetate fraction of twigs of *Lindera obtusiloba* | 1.0 | 2.5 |
| Hexane fraction of twigs of *Lindera obtusiloba* | 10.5 | >30 |

As shown in the Table 1, it can be seen that the extracts of *Lindera obtusiloba* of the present invention are excellent in the extent of inhibiting the activity of NADPH oxidases of the vascular cells. Furthermore, among the fractions, it can be seen that the n-butanol extract shows excellent effects.

Test Example 2

Measurement of Vasorelaxant Effect of Extracts of *Lindera obtusiloba* (Coronary Arteries and Aorta)

Figure 1:
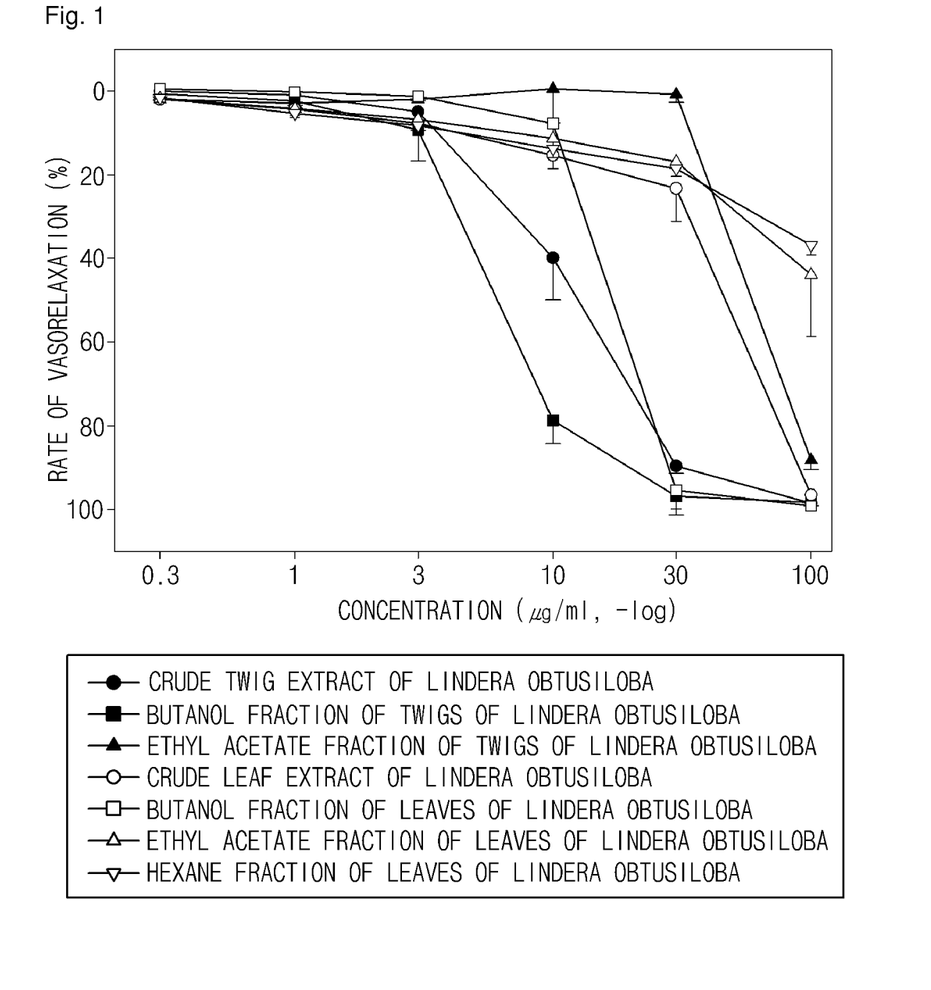
FIG. 1 is a diagram showing the measurement of the vasorelaxant activity of an extract of *Lindera obtusiloba* on swine coronary arteries.
Figure 2:
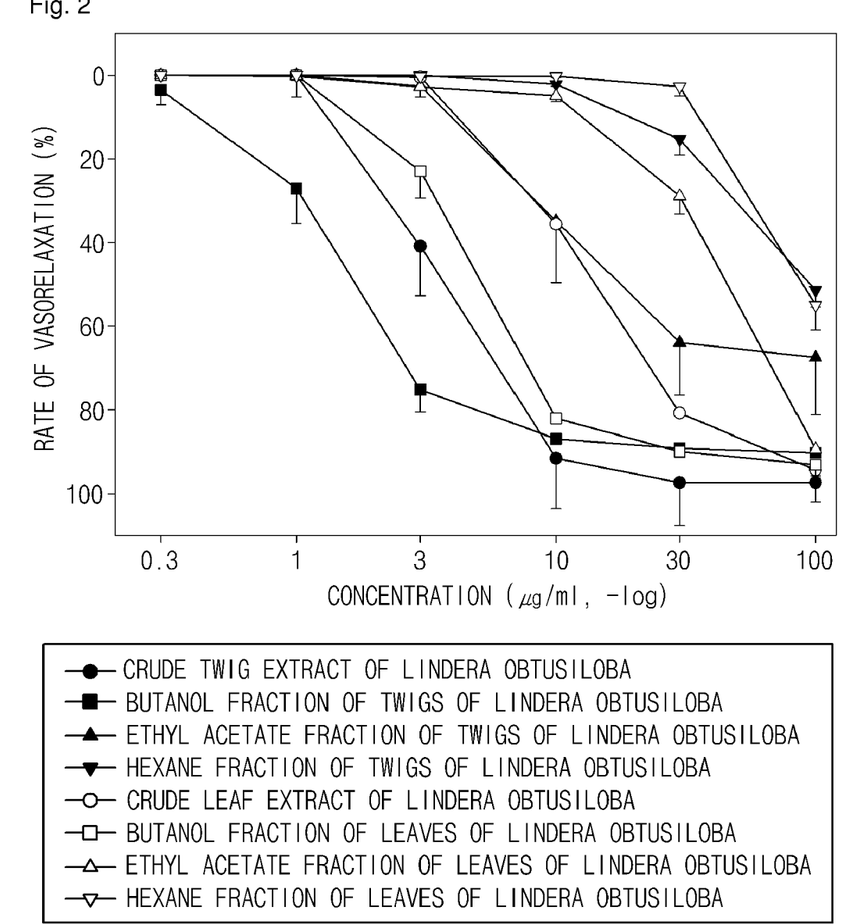
FIG. 2 is a diagram showing the measurement of the vasorelaxant activity of an extract of *Lindera obtusiloba* on the aorta of a white rat.

The vasorelaxant effects of the crude extracts and fractions of *Lindera obtusiloba* prepared in the Example 1 and Example 2 were verified. To this end, a comparison was made on the effects of relaxing the coronary arteries of a pig heart and the rat aorta, and the results are as shown in FIG. 1, FIG. 2, Table 2 (coronary arteries) and Table 3 (aorta). The coronary arteries were extracted from a pig heart purchased immediately after slaughter at the butchery. The aorta was extracted from a male SD (Sprague-Dawley) white rat, was immersed in the Krebs solution (pH 7.4) containing 18 mM NaCl, 4.7 mM KCl, 1.1 mM $MgSO_4$, 1.2 mM $KH_2PO_4$, 1.5 mM $CaCl_2$, 25 mM $NaHCO_3$, and 10 mM glucose to remove the connective tissue and fats, and then was cut into a specimen of about 3 mm in length.

The prepared coronary artery and aorta specimen were fixed in the Krebs solution at 37° C., which had been saturated with 95% $O_2$ and 5% $CO_2$ gases. The isometric tensions of the specimens were measured with a Grass physiograph (Hugo Sachs, Germany) equipped with a force-displacement transducer (Hugo Sachs, Germany). In the case of the coronary arteries, the arteries were first contracted to 80% of the maximum vascular contraction by using U46619 (1 to 60 nM), which is a thromboxane derivative. After 10 minutes therefrom, the arteries were relaxed with 300 nM Bradykinin, the safety of the vascular endothelial cells was measured, and then the arteries were washed three times with the Krebs solution to perform the experiment. The measurement of changes in the vasorelaxant effect was carried out by first contracting the arteries with the drug U46619, and then the relaxation reaction induced by the extracts of *Lindera obtusiloba* was tested in a concentration-dependent manner.

In the case of the aorta of white rat, the aorta was contracted to 80% of the maximum vascular contraction by using phenylephrine. After 15 minutes therefrom, the aorta was relaxed with 10 μM acetylcholine, the safety of the vascular endothelial cells was measured, and then the aorta was washed three times with the Krebs solution to perform the experiment. The measurement of changes in the vasorelaxant effect was carried out by first contracting the aorta with the drug phenylephrine, and then the relaxation reaction induced by the crude extracts and fraction extracts of *Lindera obtusiloba* was tested in a concentration-dependent manner. This test was repeatedly carried out using the blood vessels extracted from 5 to 10 different individuals. The ED50 value refers to the concentration (μg/ml) of the sample at which the contracted blood vessels show 50% vasorelaxation as a result of the treatment with the sample.

TABLE 2

Relaxant effect of extracts of *Lindera obtusiloba* on swine coronary arteries (unit: μg/ml)

|  | ED50 |
| --- | --- |
| Crude leaf extract of *Lindera obtusiloba* | 59.4 |
| Crude twig extract of *Lindera obtusiloba* | 12.9 |
| Butanol fraction of leaves of *Lindera obtusiloba* | 18.6 |
| Ethyl acetate fraction of leaves of *Lindera obtusiloba* | >100 |
| Hexane fraction of leaves of *Lindera obtusiloba* | >100 |
| Butanol fraction of twigs of *Lindera obtusiloba* | 6.4 |
| Ethyl acetate fraction of twigs of *Lindera obtusiloba* | 71.1 |

TABLE 3

Relaxant effect of extracts of *Lindera obtusiloba* on white rat aorta (unit: μg/ml)

|  | ED50 |
| --- | --- |
| Crude leaf extract of *Lindera obtusiloba* | 14.8 |
| Crude twig extract of *Lindera obtusiloba* | 5.0 |
| Butanol fraction of leaves of *Lindera obtusiloba* | 5.4 |
| Ethyl acetate fraction of leaves of *Lindera obtusiloba* | 48.3 |
| Hexane fraction of leaves of *Lindera obtusiloba* | 79.6 |
| Butanol fraction of twigs of *Lindera obtusiloba* | 1.7 |
| Ethyl acetate fraction of twigs of *Lindera obtusiloba* | 15.0 |
| Hexane fraction of twigs of *Lindera obtusiloba* | 95.0 |

As a result of the test, as shown in FIG. 1 and FIG. 2, the extracts of *Lindera obtusiloba* of the present invention started significant relaxation from the concentration of 1 to 10 μg/ml, and reached 94±2% relaxation at the concentration of 30 μg/ml. As shown in Table 1 and Table 2, it can be seen that the extracts of *Lindera obtusiloba* are excellent in the extent of relaxing the blood vessels of the coronary arteries and the aorta. Among the fractions, it can be seen that the n-butanol extract shows excellent effects.

Test Example 3

Test with Extracts of *Lindera obtusiloba* on Endothelial Type Nitric Oxide Synthase Activity Observations were made on the effects of the crude extracts of *Lindera obtusiloba* prepared in the Example 1 and Example 2 on the enhancement of the activity of endothelial type nitric oxide synthase. The above-mentioned effects were compared on the basis of the degree of phosphorylation of serine residue 1177 of the endothelial type nitric oxide synthase (eNOS) and serine residue 473 of Akt of bovine aortic endothelial cells. The results are presented in FIG. 3.

First, the vascular endothelial cells were mixed with DMEM (Dulbecco's minimum essential medium) and a 10% FBS (Fetal bovine serum) solution and incubated, and then the cells were incubated again for 24 hours in the culture solution with FBS excluded. After the cells were stabilized, the cells were treated with the samples at the respective concentrations, and then were allowed to react for 30 minutes. Then, the proteins were extracted and centrifuged, and the supernatant was collected to remove debris of the cells. The extracted proteins were subjected to electrophoresis on SDS-polyacrylamide gel, and then the proteins in the gel were blotted with a nitrocellulose membrane. After blocking with 3% BSA for one hour, the antibodies of phospho-eNOS and phospho-Akt (Cell Signaling, the USA) were incubated overnight at 4° C. at a ratio of 1:1,000. Subsequently, secondary antibodies diluted at a ratio of 1:2000 were treated and incubated at ambient temperature for one hour, and then the secondary antibodies were developed by chemiluminescence.

Figure 3:
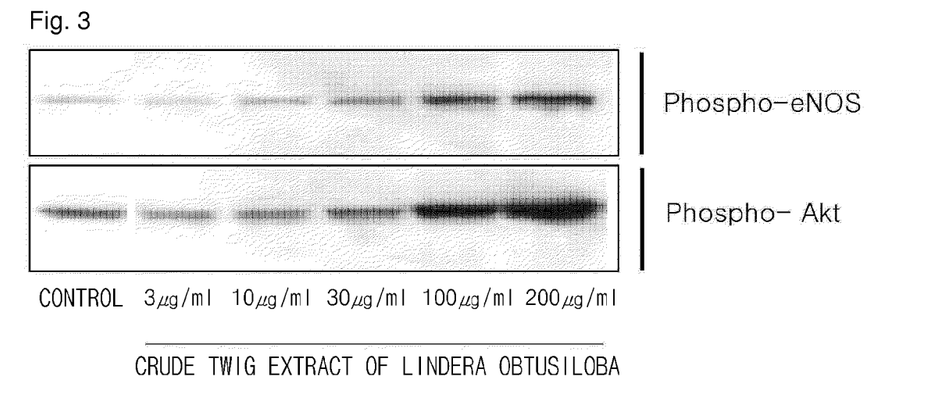
FIG. 3 is a diagram showing the measurement of the degree of activity of endothelial-type nitric oxide synthase (eNOS) and Akt protein under the action of an extract of *Lindera obtusiloba*.

As a result, as shown in FIG. 3, it can be seen that the extracts of *Lindera obtusiloba* show high effects of enhancing the activation of endothelial type nitric oxide synthase (phospho-eNOS), which produces nitric oxide, and a high degree of increase in the activation of Akt (phospho-Akt), which is an upstream regulatory factor.

Test Example 4

Test of Effects of Extracts of *Lindera obtusiloba* in Animal Model of Cardiovascular Disease The hypotensive effects in diseased animals, and the effects on the improvement of vascular oxidative stress and the improvement of endothelial dysfunction, exerted by the extracts of *Lindera obtusiloba* obtained in Example 2, were verified. To this end, a comparison was made on the extent of the effects in a disease model induced by angiotensin 2, and the results are presented in FIG. 4, FIG. 5, FIG. 6 and Table 4.

Male SD (Sprague-Dawley, 6 weeks old) white rats were purchased from Orientbio, Inc. and the rats were acclimatized for one week while freely supplying solid feedstuff and water in a small animal breeding chamber which was regulated to have a light-dark period of 12 hours. Then, the rats were arbitrarily grouped into a control group and an angiotensin 2-treated group, with each group including 6 animals. From three days before the treatment with angiotensin 2, the extracts of *Lindera obtusiloba* obtained in Example 2 were respectively suspended in 0.5% CMC (carboxymethylcellulose) at a concentration of 100 mg/kg, and the suspensions were orally administered twice a day. The control group was administered with 0.5% CMC only. Angiotensin 2 was dissolved in physiological saline at a concentration of 65 ng/min/kg, and the solution was placed in a mini-osmotic pump (Alzet Model 2002). The white rats were anesthetized, and the angiotensin 2 treatment was carried out by cutting the skin open, and inserting the mini-pump in the interscapular region. The blood pressure measurement was conducted simultaneously with the initiation of oral administration, and further measurements were made once in two days for 2 weeks, one hour after the oral administration in the morning. The specimen was heated in advance for about 10 minutes at 45 to 50° C., and then the maximum blood pressure (systolic pressure) of the tail artery was measured in a non-invasive manner by the tail-cuff plethysmography method using an automated blood pressure recording system. The heart rate was also measured at the same time.

The aorta was extracted in the same manner as in Test Example 2, and the degree of staining by DHE (dihydroethidium) and the degree of relaxation by acetylcholine were characterized to measure the extents of vascular oxidative stress and vascular endothelial dysfunction. The results were compared with the results of the control group.

TABLE 4

Hypotensive effects of extracts of *Lindera obtusiloba* (unit: mmHg)

| | 1$^{st}$ day | 7$^{th}$ day | 14$^{th}$ day |
| --- | --- | --- | --- |
| Control | 107.6 | 107.4 | 112.6 |
| Angiotensin 2 | 110.3 | 169.6 | 158.3 |
| Twig extract of *Lindera obtusiloba* | 113.9 | 129.7 | 127.4 |
| Leaf extract of *Lindera obtusiloba* | 112.5 | 144.2 | 145.4 |

As a result of the test, it can be seen from the Table that the blood pressure increase in the test animals induced by angiotensin 2 was significantly inhibited by the administration of the extracts of *Lindera obtusiloba*.

Figure 4:
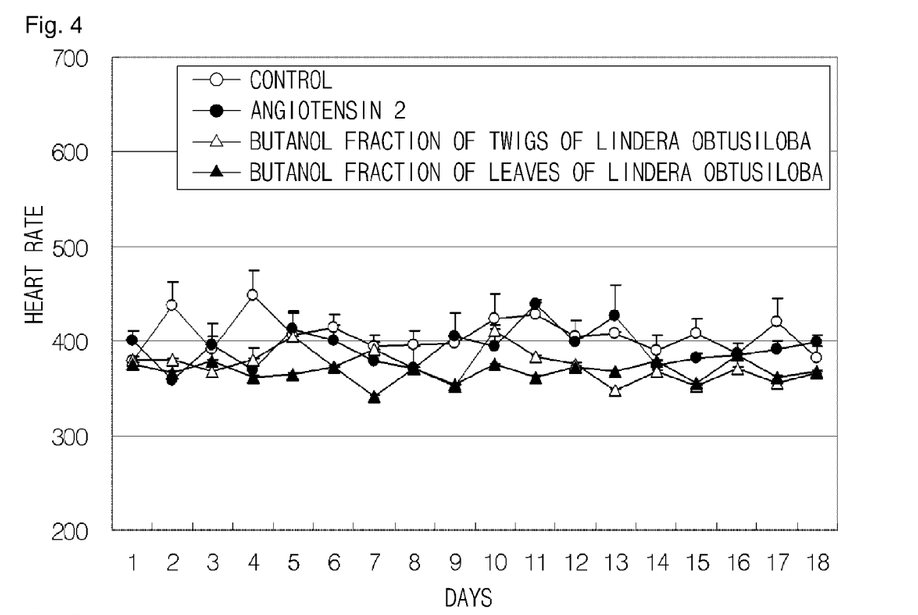
FIG. 4 is a diagram showing the measurement of the degree of influence of an extract of *Lindera obtusiloba* on the heart rate.

The increase in the heart rate was measured, and as a result, as shown in FIG. 4, it was confirmed that the extracts of *Lindera obtusiloba* do not have adverse side effects on the heart, such as tachycardia.

Figure 5:
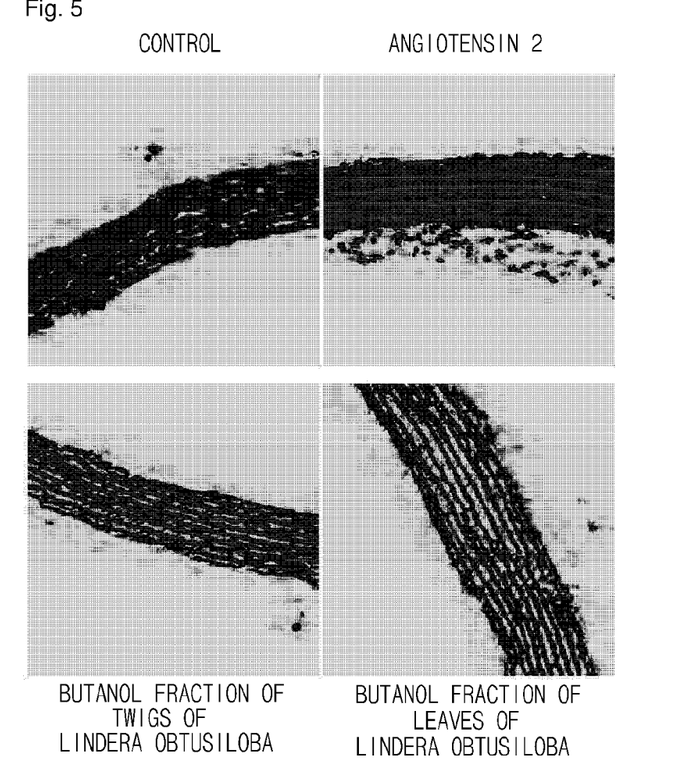
FIG. 5 is a diagram showing the measurement of the degree of decrease in vascular oxidative stress under the action of an extract of *Lindera obtusiloba*.

Furthermore, as shown in FIG. 5, it can be seen that the increase in vascular oxidative stress induced by angiotensin 2 is strongly inhibited by the administration of the extracts of *Lindera obtusiloba* (FIG. 5 is a product of black-and-white modification of a photograph which indicates the object in red and the background in black, and at the time of modification, the background was rendered white for clear distinction of the object).

The relaxation induced by 0.01 μM acetylcholine in the animals treated with angiotensin 2, was compared with that in the control group, and it was found that vascular endothelial dysfunction occurred in which relaxation does not occur smoothly (control group—27%, acetylcholine group—8%). It can be seen that such vascular endothelial dysfunction is improved by the administration of the twig extract (20%) and leaf extract (19%) of *Lindera obtusiloba*.

Test Example 5

Test on Cytotoxicity of Extracts of *Lindera obtusiloba*

Figure 6:
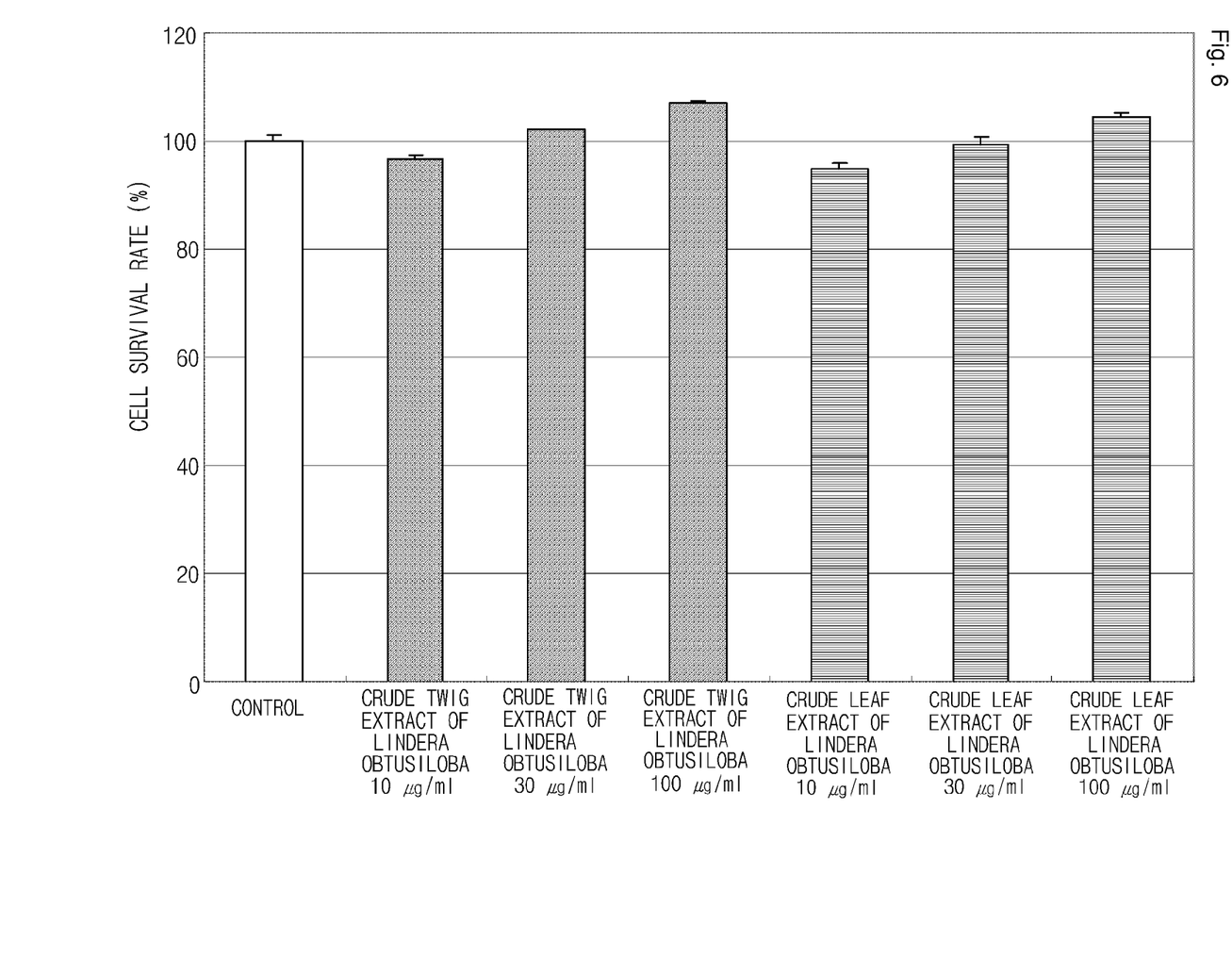
FIG. 6 is a diagram showing the measurement of the degree of cytotoxicity of an extract of *Lindera obtusiloba*.

A comparison was made for the crude extracts of *Lindera obtusiloba* prepared in the Example 1 and Example 2 on the extent of cytotoxicity, and the results are as shown in FIG. 6.

Arterial smooth muscle cells were mixed with MEM (minimum essential medium) and a 10% FBS (fetal bovine serum) solution, and the cells were incubated for 24 hours under the conditions of 5% $CO_2$/37° C. After the cells were stabilized, the cells were treated with the extracts of *Lindera obtusiloba* obtained in the Example 2, shaken, and allowed to react for 24 hours. Thereafter, the cells were incubated for one hour in the presence of an MTS solution (CellTiter 96 Aqueous One Solution, Promega), and then the absorbance at 490 nm was measured.

As shown in FIG. 6, it can be seen that the extracts of *Lindera obtusiloba* of the present invention were not found to have any influence on the survival of cells, and are very safe drugs.

Test Example 6

Statistical Processing

The significance of the test results was determined by performing the Student t-test and one-way ANOVA test with the experimental results, such that there is a significant difference in the case where p is 0.05 or less.

Preparation examples of the pharmaceutical composition and health functional food products containing the extract of the present invention will be described in the following, but the present invention is intended not to limit them, but to specifically describe them.

Preparation Example 1

Production of Powder Preparation

Powdered extract of *Lindera obtusiloba* 20 mg
Lactose 100 mg
Talc 10 mg

The components were mixed and filled in a sealed pack, and thereby a powder preparation was produced.

Preparation Example 2

Production of Tablet Preparation

Powdered extract of *Lindera obtusiloba* 10 mg
Corn starch 100 mg
Lactose 100 mg
Magnesium stearate 2 mg The components were mixed and then tableted according to a conventional tablet production method, and thereby a tablet preparation was produced.

Preparation Example 3

Production of capsule Preparation

Powdered extract of *Lindera obtusiloba* 10 mg
Crystalline cellulose 3 mg
Lactose 14.8 mg
Magnesium stearate 2 mg According to a conventional capsule production method, the components were mixed and filled in gelatin capsules, and thereby a capsule preparation was produced.

Preparation Example 4

Production of Injectable Preparation

Powdered extract of *Lindera obtusiloba* 10 mg
Mannitol 180 mg
Sterile distilled water for injection 2794 mg
$Na_2HPO_4 12H_2O$ 26 mg According to a conventional production method for injectable preparation, an injectable preparation was produced at the aforementioned component contents per ampoule (2 ml).

Preparation Example 5

Production of Liquid Preparation

Powdered extract of *Lindera obtusiloba* 10 mg
High-fructose corn syrup 10 g
Mannitol 5 g
Purified water Appropriate amount According to a conventional production method for liquid preparation, the components were added and dissolved in purified water, an appropriate amount of lemon flavor was added thereto, the components were mixed, and the total volume was adjusted to 100 ml by adding purified water. This was filled in a brown bottle and sterilized, and thereby a liquid preparation was produced.

Preparation Example 6

Production of Health Drink

Powdered extract of *Lindera obtusiloba* 10 mg
Vitamin C 15 g
Vitamin E (powdered) 100 g
Iron lactate 19.75 g
Zinc oxide 3.5 g
Nicotinic acid amide 3.5 g
Vitamin A 0.2 g
Vitamin B1 0.25 g
Vitamin B2 0.3 g
Water Appropriate amount According to a conventional production method for health drink, the components were mixed, the mixture was heated under stirring at 85° C. for about one hour, and the resulting solution was filtered. The filtrate was placed in a sterilized 2-liter container, sealed, sterilized, and refrigerated, and this was used in the production of the health drink compositions according to the present invention. In the above-given compositional ratios, components which are relatively suitable for favorite drinks were mixed and composed as a preferred Example, but the mixing ratio may be arbitrarily modified in accordance with the geographical and racial preference, such as of the class of consumers or consumer country, the uses, or the like.

The invention claimed is:

1. A pharmaceutical composition for use in treating or reducing a risk of developing a cardiovascular disease comprising an effective amount of a butanol fraction of a crude extract of *Lindera obtusiloba* as an active ingredient, wherein the cardiovascular disease is selected from the group consisting of arteriosclerosis, hypertension, vascular restenosis, peripheral vascular disease, and malfunction of endothelial cells.

2. The pharmaceutical composition according to claim 1, wherein the *Lindera obtusiloba* is selected from the group consisting of twigs, leaves and mixtures thereof.

3. The pharmaceutical composition according to claim 1, wherein the butanol fraction of the crude extract of *Lindera obtusiloba* is prepared by extraction of *Lindera obtusiloba* with a solvent selected from the group consisting of water, a $C_1$-$C_3$ lower alcohol and a mixture thereof, and re-extracting the resultant extract with butanol.

4. The pharmaceutical composition according to claim 3, wherein the solvent is a 30 to 95 wt% aqueous solution of ethanol.

5. The pharmaceutical composition according to claim 1, wherein the butanol fraction of the crude extract of *Lindera obtusiloba* has an NAD(P)H oxidase inhibitory activity.

6. The pharmaceutical composition according to claim 1, wherein the butanol fraction of the crude extract of *Lindera obtusiloba* has a vasorelaxant effect.

7. The pharmaceutical composition according to claim 1, wherein the butanol fraction of the crude extract of *Lindera obtusiloba* has an effect of increasing the activity of endothelial type nitric oxide synthase.

8. A health functional food product for use in treating or reducing the risk of developing a cardiovascular disease comprising an effective amount of a butanol fraction of a crude extract of *Lindera obtusiloba* as an active ingredient, wherein the cardiovascular disease is selected from the group consisting of arteriosclerosis, hypertension, vascular restenosis, peripheral vascular disease, and malfunction of endothelial cells.

9. The health functional food product according to claim 8, wherein the *Lindera obtusiloba* is selected from the group consisting of twigs, leaves and mixtures thereof.

10. The health functional food product according to claim 8, wherein the butanol fraction of the crude extract of *Lindera obtusiloba* is prepared by extraction of *Lindera obtusiloba* with a solvent selected from the group consisting of water, a $C_1$-$C_3$ lower alcohol and a mixture thereof, and re-extracting the resultant extract with butanol.

11. The health functional food product according to claim 8, wherein the food product is selected from beverages, chewing gum, tea and vitamin complexes.

\* \* \* \* \*